(12) United States Patent
Vanney et al.

(10) Patent No.: US 6,960,207 B2
(45) Date of Patent: Nov. 1, 2005

(54) ABLATION CATHETER HAVING A VIRTUAL ELECTRODE COMPRISING PORTHOLES AND A POROUS CONDUCTOR

(75) Inventors: Guy P. Vanney, Blaine, MN (US); Jeremy D. Dando, Plymouth, MN (US)

(73) Assignee: St Jude Medical, Daig Division, Inc., Minnetonka, MN (US)

( * ) Notice: Subject to any disclaimer, the term of this patent is extended or adjusted under 35 U.S.C. 154(b) by 0 days.

(21) Appl. No.: 10/608,297

(22) Filed: Jun. 27, 2003

(65) Prior Publication Data

US 2004/0143255 A1 Jul. 22, 2004

Related U.S. Application Data

(60) Provisional application No. 60/441,849, filed on Jan. 21, 2003.

(51) Int. Cl.⁷ .............................................. A61B 18/18
(52) U.S. Cl. ......................... 606/41; 606/49; 607/104; 607/105; 607/113
(58) Field of Search ....................... 606/27–29, 31–32, 606/41, 42, 49; 607/96, 98, 101, 104, 105, 607/113

(56) References Cited

U.S. PATENT DOCUMENTS

| | | |
|---|---|---|
| 5,348,554 A | 9/1994 | Imran et al. |
| 5,487,757 A | 1/1996 | Truckai et al. |
| 5,545,161 A | 8/1996 | Imran |
| 5,545,200 A | 8/1996 | West et al. |
| 5,785,706 A | 7/1998 | Bednarek |
| 5,826,576 A | 10/1998 | West |
| 5,906,605 A | 5/1999 | Coxum |
| 5,938,694 A | 8/1999 | Jaraczewski et al. |
| 5,993,462 A | 11/1999 | Pomeranz et al. |
| 6,080,151 A | 6/2000 | Swartz et al. |
| 6,120,500 A | 9/2000 | Bednarek et al. |
| 6,169,916 B1 | 1/2001 | West |
| 6,251,109 B1 | 6/2001 | Hassett et al. |
| 6,264,654 B1 | 7/2001 | Swartz et al. |
| 6,325,797 B1 | 12/2001 | Stewart et al. |
| 6,447,507 B1 | 9/2002 | Bednarek et al. |
| 6,522,930 B1 * | 2/2003 | Schaer et al. ................ 607/101 |
| 2003/0130713 A1 * | 7/2003 | Stewart et al. ............... 607/119 |

\* cited by examiner

Primary Examiner—Rosiland Rollins
(74) Attorney, Agent, or Firm—Heimbecher & Assoc., LLC

(57) ABSTRACT

An ablation catheter used for treatment of, for example, atrial fibrillation by electrically isolating a vessel, such as a pulmonary vein, from a chamber, such as the left atrium. The ablation catheter has a virtual electrode and a catheter shaft. The virtual electrode comprises a porous conductor. The catheter shaft includes a proximal portion and a distal portion. The distal portion includes an active region, which is either a looped structure transverse to the longitudinal axis of the catheter shaft, or a linear structure that extends parallel to the longitudinal axis of the catheter shaft. During use, the active region is directed into contact with, for example, the wall of a pulmonary vein and, upon energization, the virtual electrode creates a continuous lesion at or near the ostium of the pulmonary vein, thereby electrically isolating the pulmonary vein from the left atrium.

24 Claims, 11 Drawing Sheets

ABLATION CATHETER HAVING A VIRTUAL ELECTRODE COMPRISING PORTHOLES AND A POROUS CONDUCTOR

CROSS-REFERENCE TO RELATED APPLICATIONS

This application claims priority to U.S. Provisional Application No. 60/441,849, filed 21 Jan. 2003 (the '849 application). The '849 application is hereby incorporated by reference as though fully set forth herein. This application is related to U.S. Nonprovisional application Ser. No. 10/347,034, filed 17 Jan. 2003 (the '034 application). The '034 application is hereby incorporated by reference as though fully set forth herein.

BACKGROUND OF THE INVENTION a. Field of the Invention

This invention relates to catheters for diagnosing and treating tissue, particularly human cardiac tissue. In particular, the invention relates to an ablation catheter comprising a virtual electrode at a distal portion of the catheter to ablate tissue, the virtual electrode using energy emanating from a porous conductor contained within the distal portion.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

Catheters are also used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electrochemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the left and right ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the AV node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias," Clinical Manual of Electrophysiology, pgs. 421–431 (1993). The use of electrode catheters for ablating specific locations within the heart has also been disclosed in, for example, U.S. Pat. Nos. 4,641,649, 5,228,442, 5,231,995, 5,263,493, and 5,281,217.

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571–583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487–499 (February 1993).

Ablation of a specific location within or near the heart requires the precise placement of the ablation catheter. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

Ablation procedures using guiding introducers to guide an ablation catheter to a particular location in the heart for treatment of atrial arrhythmia have been disclosed in, for example, U.S. Pat. Nos. 5,427,119, 5,497,774, 5,564,440, 5,575,766, 5,628,316, and 5,640,955. During these procedures, ablation lesions are produced in the heart as an element of the medical procedure.

The energy necessary to ablate cardiac tissue and create a permanent lesion can be provided from a number of different sources. Originally, direct current was utilized although laser, microwave, ultrasound, and other forms of energy have also been utilized to perform ablation procedures. Because of problems associated with the use of DC current, however, radiofrequency (RF) has become the preferred source of energy for ablation procedures. The use of RF energy for ablation has been disclosed, for example, in U.S. Pat. Nos. 4,945,912, 5,242,441, 5,246,438, 5,281,213, 5,281,218, and 5,293,868. The use of RF energy with an ablation catheter contained within a transseptal sheath for the treatment of W-P-W in the left atrium is disclosed in Swartz, J. F. et al., "Radiofrequency Endocardial Catheter Ablation of Accessory Atrioventricular Pathway Atrial Insertion Sites," Circulation, Vol. 87, pgs. 487–499 (1993). See also Tracey, C. N., "Radio Frequency Catheter Ablation of Ectopic Atrial Tachycardia Using Paced Activation Sequence Mapping," J. Am. Coll. Cardiol. Vol. 21, pgs. 910–917 (1993).

In addition to radiofrequency ablation catheters, thermal ablation catheters have been disclosed. During thermal ablation procedures, a heating element, secured to the distal end of a catheter, heats thermally conductive fluid, which fluid then contacts the human tissue to raise its temperature for a sufficient period of time to ablate the tissue. A method and device for thermal ablation using heat transfer is disclosed in U.S. Pat. No. 5,433,708. Another thermal ablation procedure utilizing a thermal electrode secured to a catheter and located within a balloon with openings in that balloon to permit heated conductive fluid introduced into the balloon from the catheter to escape from the balloon for contact with the tissue to be ablated is disclosed in U.S. Pat. No. 5,505,730.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes as disclosed in, for example, U.S. Pat. Nos. 4,892,102, 5,228,442, 5,327,905, 5,354,297, 5,487,385, and 5,582,609.

To form linear lesions within the heart using a conventional ablation tip electrode requires the utilization of procedures such as a "drag burn." The term "linear lesion" as used herein means and elongate, continuous lesion, whether straight or curved, that blocks electrical conduction. During a "drag burn" procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, unablated tissue or incompletely ablated tissue may remain electrically active, permitting the continuation of the stray circuit that causes the arrhythmia.

It has been discovered that more efficient ablation may be achieved if a linear lesion of cardiac tissue is formed during a single ablation procedure. The production of linear lesions in the heart by use of an ablation catheter is disclosed in, for example, U.S. Pat. Nos. 5,487,385, 5,582,609, and 5,676,662. A specific series of linear lesions formed in the atria for the treatment of atrial arrhythmia are disclosed in U.S. Pat. No. 5,575,766.

The ablation catheters commonly used to perform these ablation procedures produce electrically inactive or noncontractile tissue at a selected location by physical contact of the cardiac tissue with an electrode of the ablation catheter. Conventional tip electrodes with adjacent ring electrodes cannot perform this type of procedure, however, because of the high amount of energy that is necessary to ablate sufficient tissue to produce a complete linear lesion. Also, conventional ring electrode ablation may leave holes or gaps in a lesion, which can provide a pathway along which unwanted circuits can travel.

An ablation catheter for use in the heart that contains a pair of intertwined helical electrodes is disclosed in U.S. Pat. No. 5,334,193. The helically wound electrode is affixed to the surface of the catheter body over a distance of about eight centimeters from the distal tip of the catheter body. Other helical electrodes are disclosed in U.S. Pat. Nos. 4,161,952, 4,776,334, 4,860,769, 4,934,049, 5,047,026, 5,542,928, and WO 95/10319.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode, which often results in the formation of coagulum on the electrode, which reduces the efficiency of the ablation electrode. With direct contact between the electrode and the blood, some of the energy targeted for the tissue ablation is dissipated into the blood.

To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

In some instances, stray electrical signals find a pathway down the pulmonary veins and into the left atrium of the heart. In these instances, it may be advantageous to produce a circumferential lesion at or near the ostium of one or more of the pulmonary veins. Desirably, such a circumferential lesion would electrically isolate a pulmonary vein from the left atrium, completely blocking stray signals from traveling down the pulmonary vein and into the left atrium. It is desirable to have a catheter with a distal portion for forming such circumferential lesions in tissue while avoiding problems with existing designs.

BRIEF SUMMARY OF THE INVENTION

It is an object of the disclosed invention to provide an improved ablation catheter for forming linear lesions in tissue, including tissue within the human heart and at or near the ostium of the pulmonary veins. This and other objects are provided by the ablation catheter that is disclosed by the present invention.

In a first form, the instant invention is an ablation catheter for treating tissue. The ablation catheter comprises a porous conductor adapted to deliver therapeutic energy (e.g., the porous conductor may be connected to an RF generator) and a catheter shaft. The catheter shaft has a proximal portion and a distal portion. The distal portion comprises at least one lumen (which is adapted to carry wires, optical fibers, and fluids for a variety of functional purposes) and an active region. The porous conductor is attached within the at least one lumen, and the active region is adapted to introduce the therapeutic energy from the porous conductor to the tissue. The catheter shaft may be constructed from a polymer, and the porous conductor may be constructed from metal.

In another form, the instant invention is a catheter for ablating tissue and, in one form, comprises a catheter shaft and a mesh or woven electrode. The mesh or woven electrode is adapted to be connected to an ablation energy supply (e.g., an RF generator). The catheter shaft has a proximal portion, a distal portion, and at least a first lumen that extends from the proximal portion to the distal portion. The distal portion is adapted to be inserted into a body cavity having tissue to be ablated and may be straight or curved. The distal portion comprises an active region that includes at least one porthole. The first lumen is adapted to carry a conductive fluid medium from the proximal portion to the portholes along the active region of the distal portion. The mesh or woven electrode is mounted within the first lumen over the plurality of portholes and extends along the active region of the distal portion, and the mesh or woven electrode is adapted to supply the ablation energy to the tissue through the conductive fluid medium.

In yet another form, the instant invention is again a catheter for ablating tissue and comprises a catheter shaft and a mesh electrode. The catheter shaft comprises a proximal portion, a distal portion, a first lumen, and a second lumen. The distal portion comprises at least one curved section adapted to be inserted into a body cavity having tissue to be ablated. The at least one curved section defines an inner peripheral wall and an outer peripheral wall, and the outer peripheral wall has an active region that includes a plurality of portholes. The first lumen extends from the proximal portion to the distal portion, and the first lumen is adapted to carry a conductive fluid medium from the proximal portion to the portholes along the active region of the distal portion. The second lumen extends adjacent to the inner peripheral wall. The mesh electrode is mounted within the first lumen over the plurality of portholes and extends along the active region of the distal portion. The mesh electrode is adapted to supply ablation energy through the conductive fluid medium. A shape retention wire is mounted in the second lumen.

In another form of the instant invention, the cross-sectional configuration of the active region of the distal portion is adapted to bias the active region against the tissue to be ablated. Thus, the cross-sectional configuration along the active region may comprise a flattened outer peripheral wall. Such cross-sectional configurations include polygonal configurations. As used herein, a "polygonal configuration" may include a curved line segment or a curved side. Thus, D-shaped, triangular, or rectangular cross-sectional configurations are all polygonal configurations as that term is used herein. Cross-sectional configuration having a flattened outer peripheral wall may also include, for example, elliptical configurations.

A more detailed explanation of the invention is provided in the following description and claims, and is illustrated in the accompanying drawings.

DETAILED DESCRIPTION OF THE INVENTION

Figure 1:
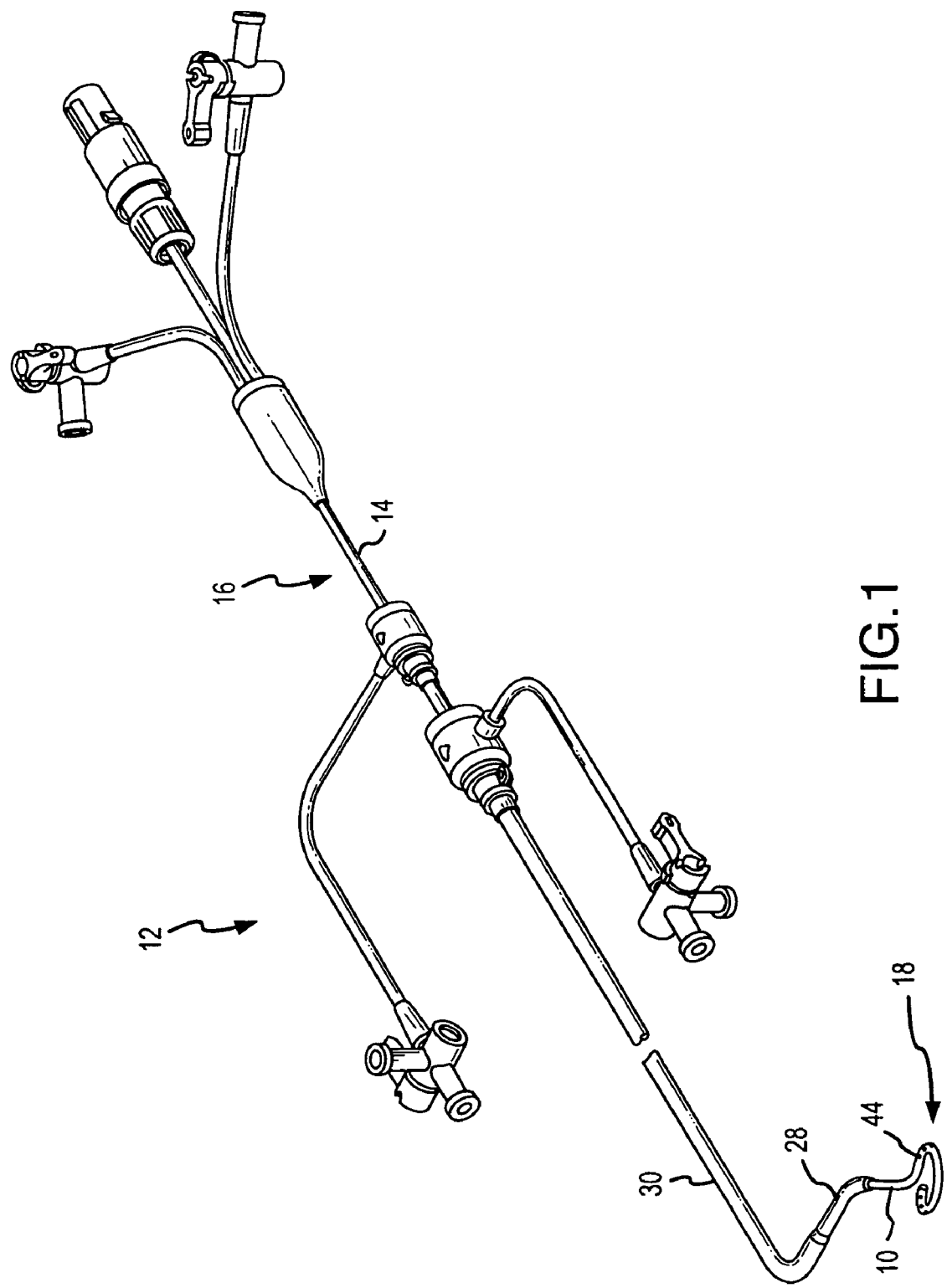
FIG. 1 is an isometric view of an ablation catheter assembly including an ablation catheter according to a first embodiment of the present invention.

In general, the instant invention relates to an ablation catheter 10, which may comprise part of an ablation catheter assembly 12, wherein the ablation catheter 10 comprises a catheter shaft 14 having a proximal portion 16 and a unique distal portion 18 (see, e.g., FIGS. 1–3) or 18' (see, e.g., FIGS. 6–8) for ablating tissue 20 (see, e.g., FIG. 11) using energy 22 emanating from a porous conductor (e.g., mesh or woven) 24 (see, e.g., FIGS. 3–5) or 24' (see, e.g., FIG. 8) attached within the ablation catheter 10, and/or wherein the distal portion of the ablation catheter 10 may have a cross-sectional configuration that is adapted to bias the catheter into a desired orientation which places a flattened outer peripheral wall 26, 26' (see, e.g., FIGS. 13–15) of an active region 38 (see, e.g., FIGS. 2 and 3) or 38' (see, e.g., FIG. 6) of the catheter against the tissue 20 to be ablated. As used herein, "flattened" outer peripheral walls encompasses more than merely "flat" outer peripheral walls. For example, some oval or elliptical configurations have at least one flattened wall within the meaning of that term as used herein. The catheter shaft 14 may be constructed from a number of different polymers (e.g., polyurethane, polypropylene, oriented polypropylene, polyethylene, crystallized polyethylene terephthalate, polyethylene terephthalate, polyester, polyvinyl chloride, etc.).

Figure 6:
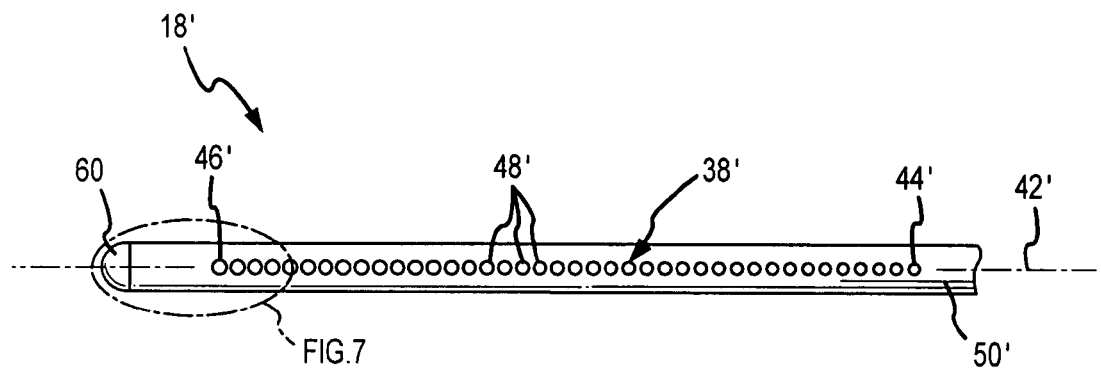
FIG. 6 is a fragmentary view of a distal portion of an ablation catheter according to a second embodiment of the present invention, wherein the active region of the ablation catheter is straight.
Figure 7:
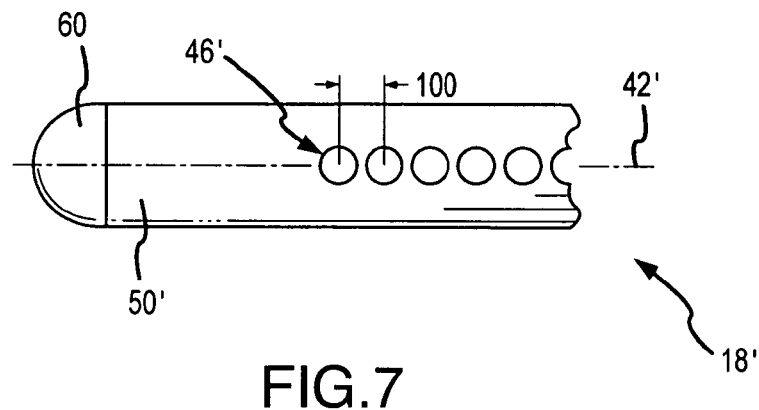
FIG. 7 is an enlarged, fragmentary view of a portion of the ablation catheter depicted in FIG. 6.
Figure 8:
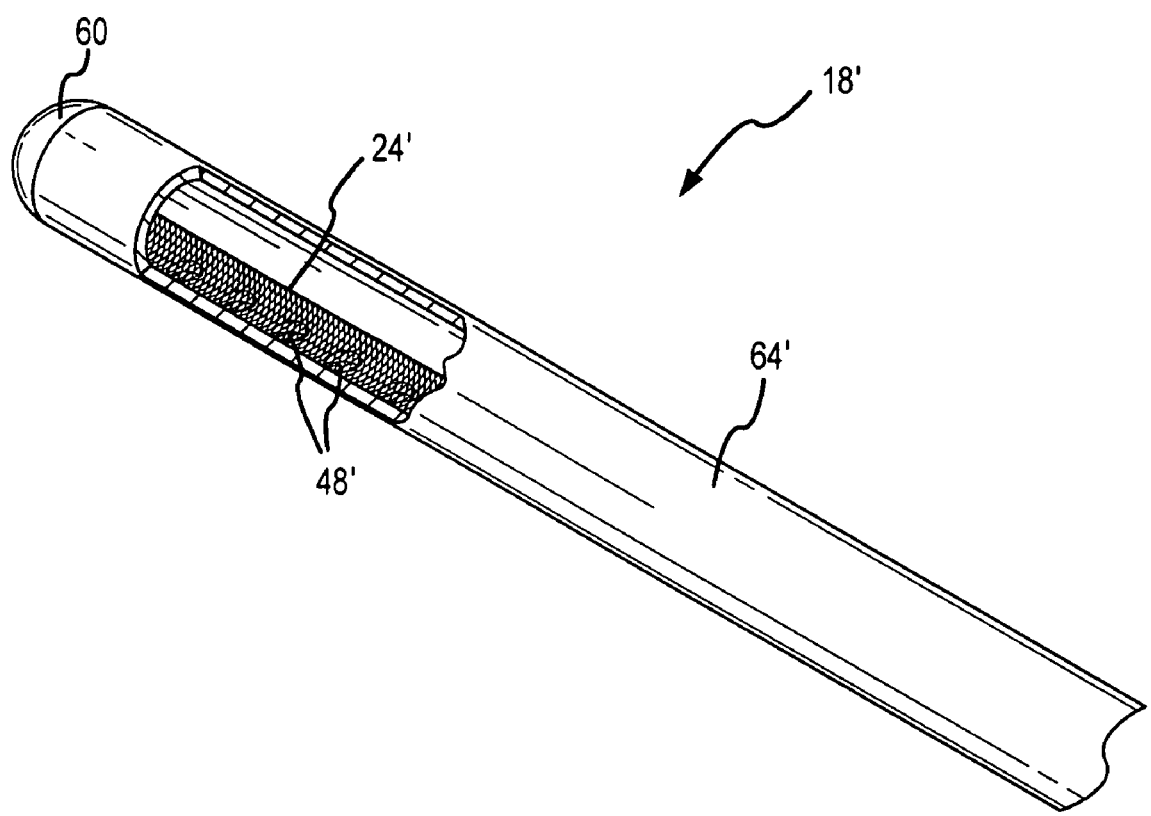
FIG. 8 is a fragmentary, isometric view of the distal portion of the ablation catheter depicted in FIGS. 6 and 7, with a portion of an inner peripheral wall broken away to reveal a porous conductor positioned over the plurality of portholes.

FIG. 1 is an isometric view looking downwardly at an ablation catheter assembly 12 having an ablation catheter 10 according to a first embodiment of the present invention. In the first embodiment, the distal portion 18 of the ablation catheter 10 is curved (see also, e.g., FIGS. 2–5). As depicted in FIG. 1, the ablation catheter 10 may be used in combination with an inner guiding introducer 28 and an outer guiding introducer 30. Alternatively, a single guiding introducer may be used or a precurved transseptal sheath may be used instead of one or more guiding introducers. In general, the guiding introducer, the guiding introducers, or the precurved sheath are shaped to facilitate placement of the ablation catheter 10 at the tissue 20 to be ablated. Thus, for example, the introducer or the introducers or the transseptal sheath make it possible to navigate to the heart 32 and through its complex physiology to reach specific tissue to be ablated. FIGS. 6–8 depict a second embodiment of an ablation catheter 10 according to the present invention.

As shown in FIGS. 1–8, the ablation catheter 10 according to the present invention may have a curved distal portion 18 (see, e.g., FIGS. 1–3) or a straight distal portion 18' (see, e.g., FIGS. 6–8). The distal portion, whether curved or straight, includes one or more lumens 34, 36 to carry wires, optical fibers, or fluids (e.g., a conductive fluid or a radiopaque fluid) for a variety of functional purposes, and an active region 38 (see, e.g., FIGS. 2 and 3) or 38' (see, e.g., FIG. 6) that performs the actual ablation of tissue. The wires that may be present in the lumens may include, for example, metallic or nonmetallic wires that provide support or that enhance the positionability of the distal portion (e.g., shape retention wires 40 (see, e.g., FIGS. 3 and 4) or shape memory wires or super elastic wires). The wires may also be used for conducting diagnostic electrical signals from the distal portion or therapeutic energy to the distal portion. In both of the embodiments, a plurality of portholes 44–48 (FIGS. 2–5 and FIGS. 6–8) extend along a porthole centerline 42 (see, e.g., FIG. 2) or 42' (see, e.g., FIGS. 6 and 7) in the active region 38 (see, e.g., FIG. 2) or 38' (see, e.g., FIG. 6). The portholes include a most proximal or first porthole 44 (see, e.g., FIG. 3) or 44' (see, e.g., FIG. 6), a most distal or last porthole 46 (see, e.g., FIGS. 2 and 3) or 46' (see, e.g., FIGS. 6 and 7), and a plurality of intermediate portholes 48 (see, e.g., FIGS. 2–5) or 48' (see, e.g., FIGS. 6–8). The porthole centerline 42, 42' extends along an outer peripheral wall 50 (see, e.g., FIGS. 3–5) or 50' (see, e.g., FIGS. 6 and 7) of the distal portion, parallel to the longitudinal axis 52 (see, e.g., FIG. 12), 52' (see, e.g., FIGS. 13 and 14), or 52" (see, e.g., FIG. 15) of the portion of the ablation catheter defining the active region.

As shown in FIGS. 1–5, in the first embodiment of the ablation catheter 10, the distal portion 18 comprises a first curved section 54, a second curved section 56, and a third curved section 58, which together comprises a unitary component in this embodiment, but which could comprise separate pieces that have been joined together. A rounded tip 60, which may be an ablation electrode, is clearly visible in FIGS. 2 and 3. The catheter shaft 14, which is typically a braided shaft, includes a "straight" section 62 (see, e.g., FIG. 2) that follows a circuitous path from the location of the distal portion 18 of the catheter shaft 14, which is adjacent to the tissue to be ablated, to the proximal portion 16 of the catheter shaft 14, which is outside of the body containing the tissue to be ablated. The straight section 62 is joined to the distal portion 18. In this first embodiment, the third curved section 58 comprises the active region 38. As shown to good advantage in FIGS. 2 and 3, in the first embodiment the active region 38 is along a radial apex of the outer peripheral wall 50, along the porthole centerline 42. The active region 38 of the distal portion 18 is the portion that includes the plurality of portholes 44–48 that are placed against the tissue 20 to be ablated (e.g., the inner wall of a pulmonary vein).

Figure 2:
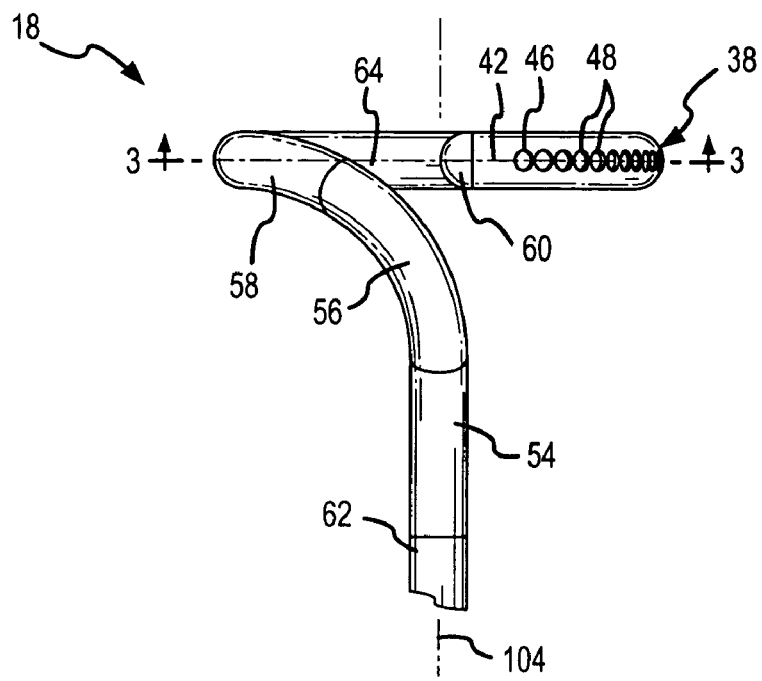
FIG. 2 is a fragmentary view of a distal portion of the ablation catheter according to the first embodiment of the present invention, wherein the active region of the catheter is curved.
Figure 3:
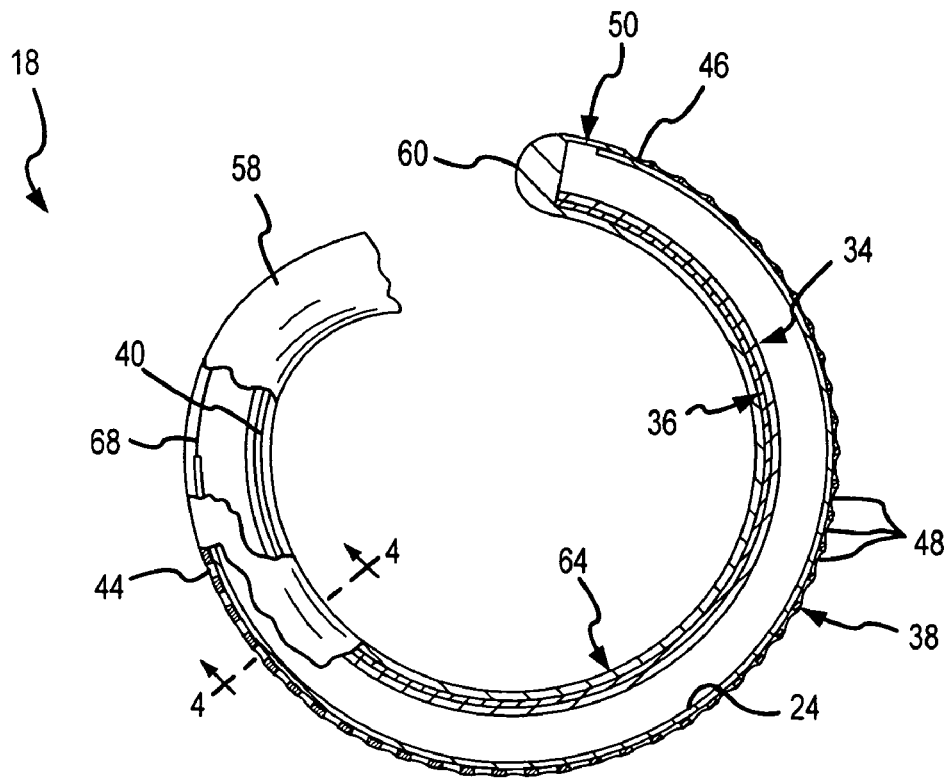
FIG. 3 is a fragmentary view of an ablation catheter according to a first variant of the first embodiment of the present invention, taken along line 3—3 of FIG. 2, wherein pieces of the ablation catheter wall have been broken away to reveal internal features of a bi-lumenal distal portion.
Figure 4:
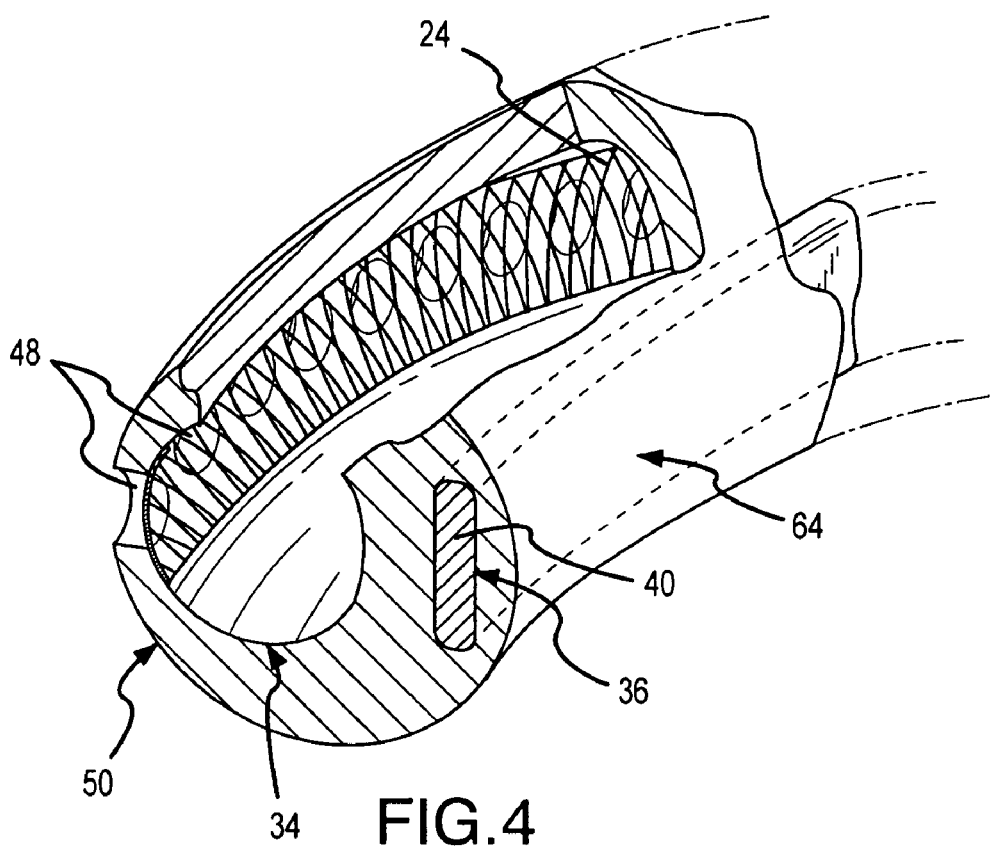
FIG. 4 is an enlarged, fragmentary, isometric view taken along line 4—4 of FIG. 3 with pieces of the ablation catheter wall broken away to reveal the configuration of the bi-lumenal distal portion, with a section of porous conductor in a first lumen over a plurality of portholes, and a shape retention wire in a second lumen.

FIGS. 3 and 4 depict a first variant of the first embodiment of the ablation catheter 10 depicted in FIGS. 1 and 2. In this first variant of the first embodiment, the ablation catheter 10 is a virtual electrode ablation catheter having a bi-lumenal distal portion 18, including a first lumen 34 adjacent to the outer peripheral wall 50 and a second lumen 36 adjacent to an inner peripheral wall 64. FIG. 3 is a fragmentary view of the distal portion 18 of the ablation catheter taken along line 3—3 of FIG. 2, wherein pieces of the ablation catheter wall have been broken away to reveal internal features of the bi-lumenal distal portion 18. FIG. 4 is an enlarged, fragmentary, isometric view taken along line 4—4 of FIG. 3 with pieces of the ablation catheter wall broken away. As clearly shown in FIGS. 3 and 4, the first variant of the first embodiment includes a porous conductor 24 (e.g., a metal mesh or woven electrode) mounted on the inside of the first lumen 34 over the plurality of portholes 44–48, thereby forming a porous fluid distribution manifold. The second lumen 36 in the embodiment of FIGS. 3 and 4 includes a shape retention wire 40 (e.g., a Nitinol or NiTi wire). The first lumen 34 is adapted to carry a conductive fluid medium 66 (e.g., hypertonic saline) during use of the ablation catheter. The conductive fluid medium may be seen in, for example, FIG. 11. An electrical lead 68 supplies ablation energy 22 to the porous conductor 24. This electric lead 68 has one end connected to the porous conductor 24 at the distal portion 18 of the ablation catheter 10, and its opposite end connected to an energy source (not shown) in a known manner, at the proximal portion 16 of the ablation catheter assembly 12 depicted in FIG. 1.

Figure 5:
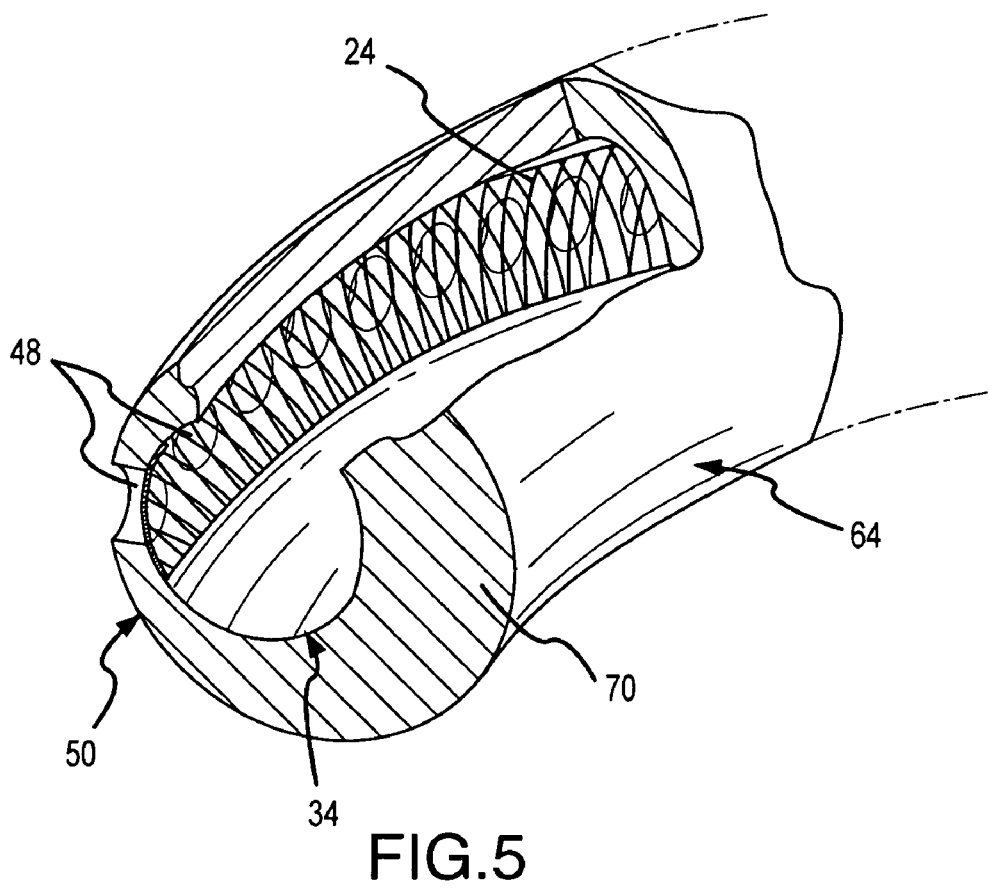
FIG. 5 is similar to FIG. 4, but depicts an ablation catheter according to a second variant of the first embodiment of the present invention, with a distal portion having a single lumen carrying the porous conductor.

FIG. 5 depicts a second variant of the first embodiment of an ablation catheter according to the present invention. In this second variant, the distal portion of the ablation catheter has only a first lumen 34. In this particular variant of the first embodiment, the distal portion of the ablation catheter may be either manufactured from materials that sufficiently retain a desired configuration, possibly attributable to one or more thickened areas 70, or it is unnecessary for the distal portion of the ablation catheter to hold a specific configuration.

FIGS. 6–8 depict a fragmentary view of the distal portion 18' of the ablation catheter 10, according to the second embodiment of the present invention, wherein the ablation catheter 10 again is a virtual electrode ablation catheter. The active region 38' of the ablation catheter according to the second embodiment is straight. In FIG. 8, which is a fragmentary, isometric view of the second embodiment of the distal portion of the ablation catheter according to the present invention, a piece of the inner peripheral wall 64' has been broken away to reveal a porous conductor 24' in position over the portholes 48'. In this second embodiment of the distal portion 18' of the ablation catheter 10 according to the present invention, the ablation catheter 10 has at least one lumen in which conductive fluid medium can flow from the proximal portion of the ablation catheter to the distal portion of the ablation catheter. The conductive fluid medium would flow through the porous conductor 24' and exit the distal portion 18' of the ablation catheter 10 through the plurality of portholes 44'–48' as discussed further below. A rounded tip 60, which may be an ablation electrode, may also be seen in FIGS. 6–8.

The porous conductor 24 (see, e.g., FIGS. 3–5) or 24' (see, e.g., FIG. 8) may be mounted (e.g., bonded or frictionally fit) in the ablation catheter 10 after it is formed, or the ablation catheter 10 may be formed around the porous conductor. If the porous conductor is mounted in a formed ablation catheter, a tapered mandrel may be used to place the porous conductor into, and conform it to, the interior configuration of the appropriate lumen. The portholes may be formed (e.g., molded or drilled) before or after the porous conductor is mounted. The porous conductor may overlay the entire inner surface or less than the entire inner surface of the lumen in which the porous conductor is mounted.

Figure 9:
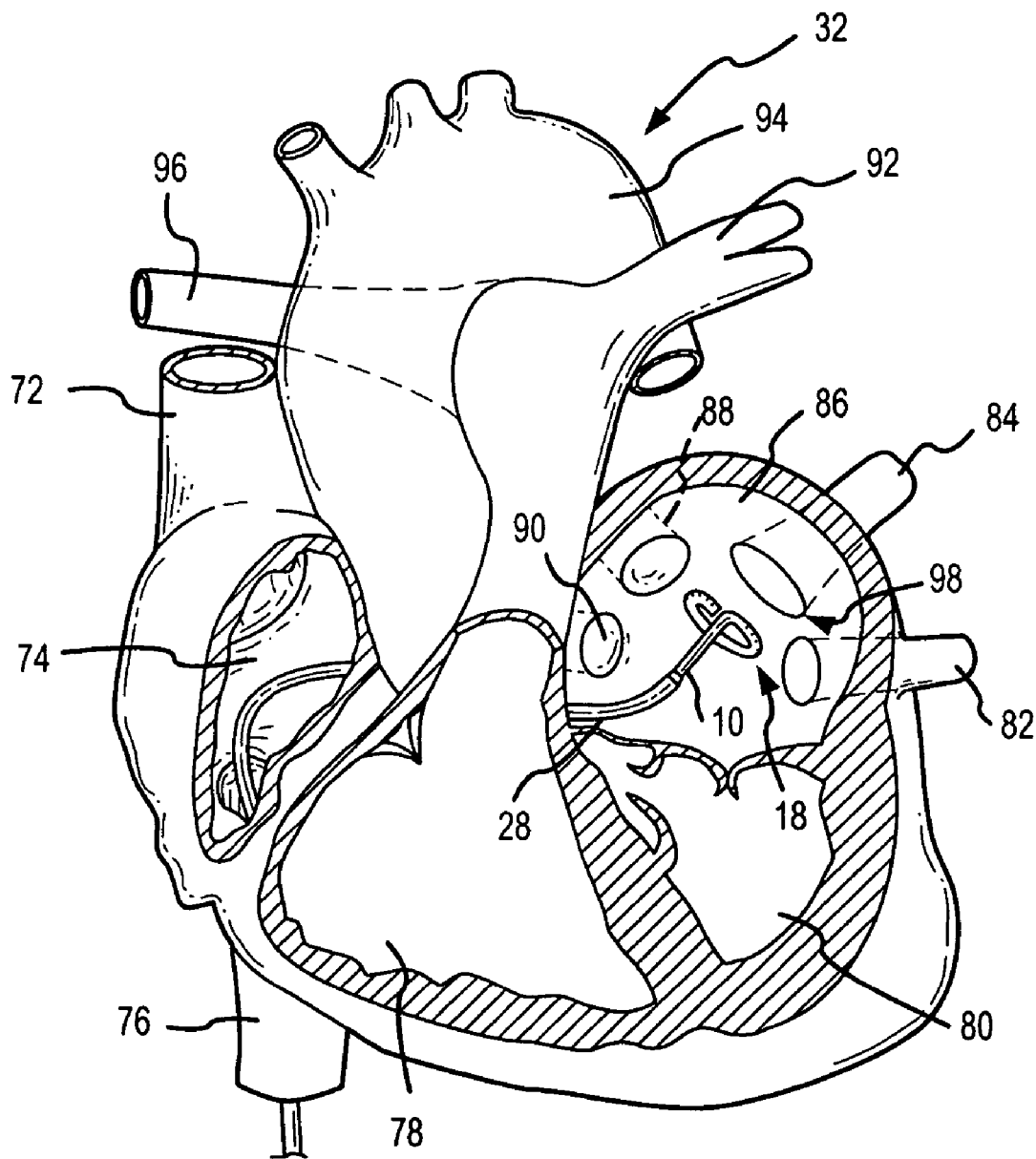
FIG. 9 is an isometric view of a heart with portions of the atria and ventricles broken away to reveal positioning of the ablation catheter depicted in, for example, FIGS. 1–4 (or the ablation catheter depicted in FIG. 5) in the left atrium, adjacent to the left superior pulmonary vein.
Figure 10:
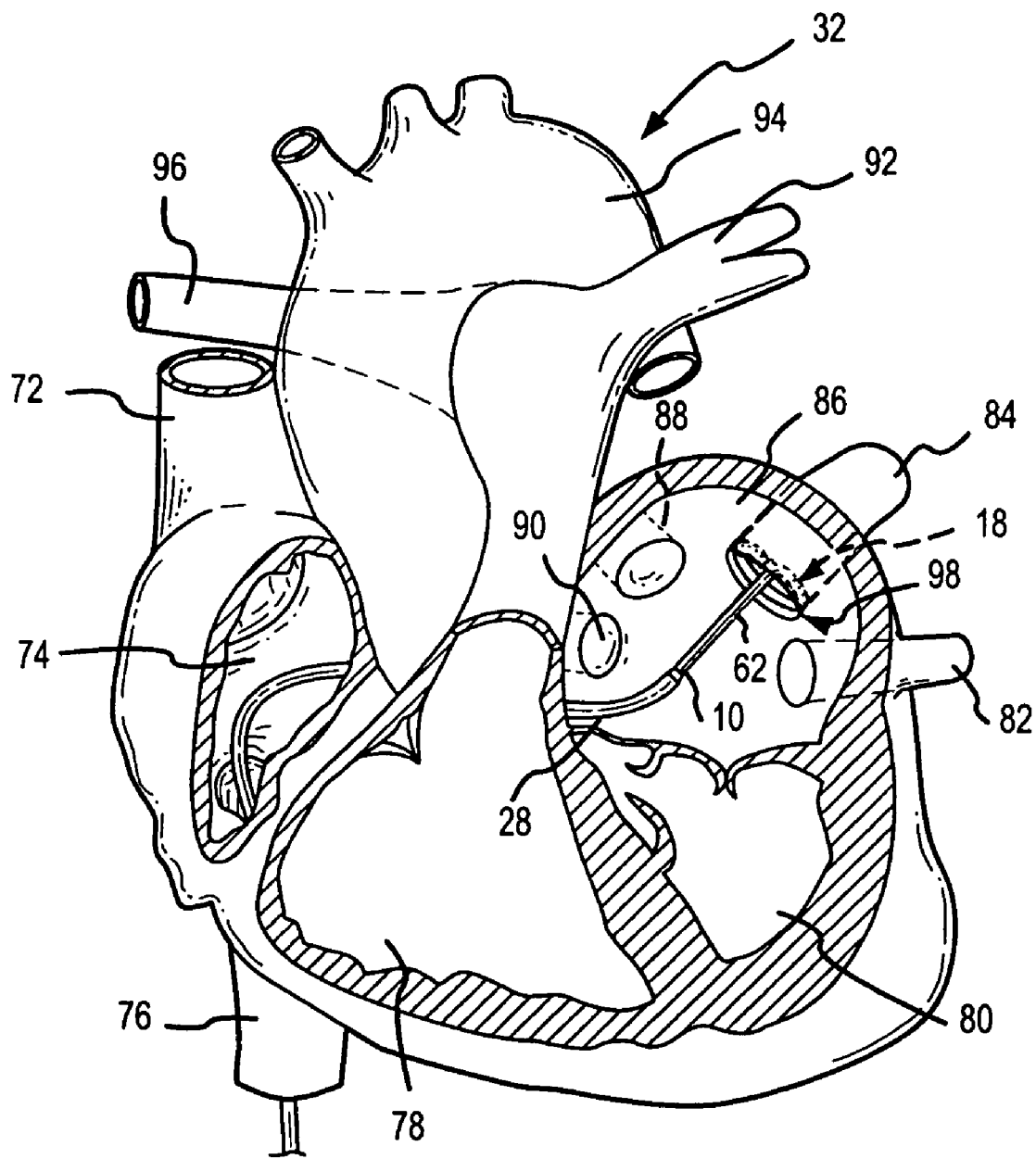
FIG. 10 is similar to FIG. 9, but depicts the ablation catheter in position near the ostium of the left superior pulmonary vein.

Remaining FIGS. 9–19 depict the ablation catheter 10 according to the present invention in use, for example, ablating tissue in a pulmonary vein. FIGS. 9 and 10 depict a number of primary components of the heart 32 to orient the reader. In particular, starting in the upper left hand portion of FIGS. 9 and 10, and working around the periphery of the heart in a counterclockwise direction, the following parts of the heart are depicted: superior vena cava 72, right atrium 74, inferior vena cava 76, right ventricle 78, left ventricle 80, left inferior pulmonary vein 82, left superior pulmonary vein 84, left atrium 86, right superior pulmonary vein 88, right inferior pulmonary vein 90, left pulmonary artery 92, arch of aorta 94, and right pulmonary artery 96.

The distal portion 18 of the ablation catheter 10 according to the first embodiment, for example, is positioned adjacent to the ostium 98 of the left superior pulmonary vein 84 (see FIG. 9) using known procedures, like the "Seldinger technique," wherein the right venous system may be first accessed as follows. A peripheral vein (such as a femoral vein) is punctured with a needle, the puncture wound is dilated with a dilator to a size sufficient to accommodate a guiding introducer or transseptal sheath. The guiding introducer or transseptal sheath with at least one hemostasis valve (see FIG. 1) is seated within the dilated puncture wound while maintaining relative hemostasis. With the guiding introducer or transseptal sheath in place, the ablation catheter 10 is introduced through the hemostasis valve of the guiding introducer or transseptal sheath and is advanced along the peripheral vein, into the region of the vena cava (e.g., the inferior vena cava 76), and into the right atrium 74. From there, the ablation catheter 10, together with its guiding introducer or transseptal sheath is further advanced through a hole in the interatrial septum, which a doctor would make before inserting the ablation catheter 10 into the guiding introducer or transseptal sheath, and into the left atrium 86. Once the guiding introducer or transseptal sheath is in the left atrium 86, it can be advanced to the respective positions depicted in FIGS. 9 and 10. The ablation catheter 10 can either be advanced until the active region 38 of the distal portion 18 extends from the guiding introducer or the transseptal sheath, or the guiding introducer or the transseptal sheath can be retracted to expose the distal portion 18 of the ablation catheter 10. In FIG. 10, the distal portion 18 of the ablation catheter 10 according to the first embodiment is near the ostium 98 of the left superior pulmonary vein 84.

Figure 11:
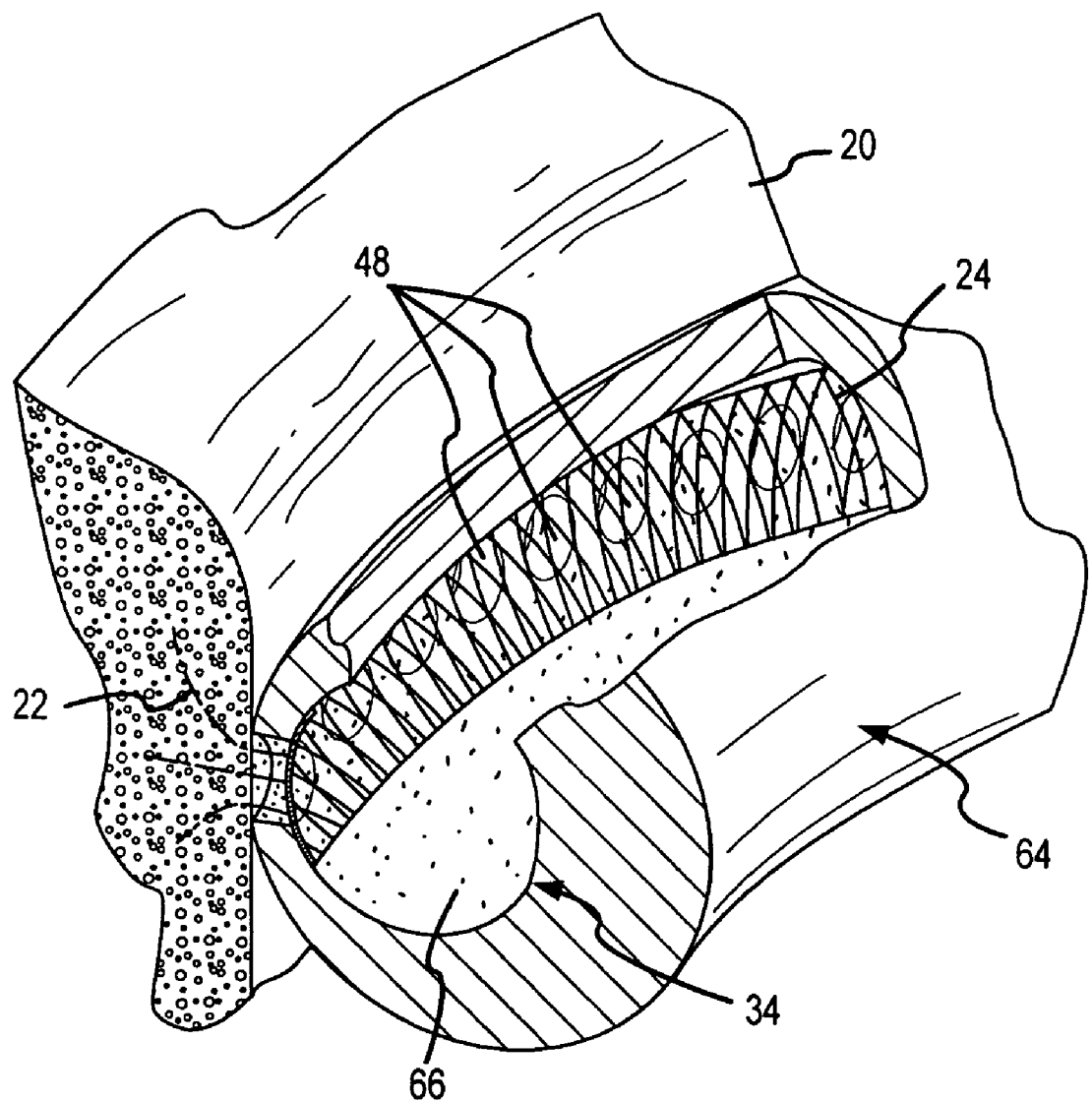
FIG. 11 is a fragmentary, isometric view similar to FIG. 5, but wherein the active region of the ablation catheter is in position against tissue to be ablated, and wherein a conductive fluid medium is present in the first lumen, and wherein RF energy is being supplied to the tissue by the porous conductor.

While the distal portion 18 of the ablation catheter 10 is near the ostium 98 of the left superior pulmonary vein 84 as depicted in FIG. 10, the porous conductor 24 (see, e.g., FIGS. 3–5) is activated to create a desired lesion. As shown in FIG. 11, during activation of the ablation catheter, a conductive fluid medium 66 is flowing through the first lumen 34, past the porous conductor 24, and out of the portholes 44–48. The porous conductor 24, when the ablation catheter is active, delivers ablation energy 22 (e.g., radiofrequency or RF energy) to the tissue 20 via the conductive fluid medium 66. The RF energy 22 emanating from the porous conductor 24 passes through the conductive fluid medium 66 contained in the first lumen 34, through the portholes 44–48, and into the adjacent tissue 20. Thus, when the ablation catheter 10 is operating with conductive fluid medium 66 flowing through the porous conductor 24 and out of the portholes 44–48, the ablation energy 22 is delivered directly to the tissue 20 through the portholes 44–48. In this embodiment, a lesion is formed in the tissue 20 by the RF energy 22. Lesion formation may also be facilitated or enhanced by the conductive fluid medium 66, which convectively cools the surface of the tissue 20 while the ablation energy 22 is being delivered below the surface of the tissue. This inhibits excess damage to the surface of the tissue 20 while also reducing the amount of coagulum formed. The RF energy 22 is conducted into the adjacent tissue 20 while the conductive fluid medium 66 convectively cools the surface of the tissue 20.

In order for the ablation catheter to form a sufficient lesion, it is desirable to raise the temperature of the tissue to at least 50–60° C. for an appropriate length of time. Thus, sufficient RF energy must be supplied to the porous conductor to produce this lesion-forming temperature in the adjacent tissue for the desired duration. When the flow rate of the conductive fluid medium is appropriately regulated, the conductive fluid medium flows at a sufficient rate to avoid stagnation or re-circulation and to push blood away from the gap between the catheter and the tissue. The flow rate should be high enough to prevent or minimize vaporization of the conductive fluid medium since such vaporization can inhibit delivery of ablation energy to the tissue. As previously mentioned, the distal portion of the ablation catheter forms the lesion by direct conduction of ablation energy from the porous conductor through the conductive fluid medium and into the tissue.

The conductive fluid medium flowing through the porous conductor and portholes prevents blood from flowing into the distal portion of the ablation catheter and pushes blood from the area adjacent to the portholes. This helps prevent formation of coagulum, which can have undesirable effects on the patient. As mentioned above, the conductive fluid medium is caused to flow at a rate that prevents the electrode from overheating the conductive fluid medium and producing vapor in the first lumen. If the conductive fluid medium were to boil, creating vapor, the ablation catheter's ability to form a desired lesion in the adjacent tissue may be greatly reduced or inhibited since the ablation energy may be unable to reach the tissue in sufficient quantity. Thus, the flow of conductive fluid medium through the first lumen, the porous conductor, and out of the portholes is managed or regulated so that there is sufficient flow to prevent vaporization, but not so much flow that the gap between the catheter and the tissue opens, prohibiting the porous conductor from being able to deliver sufficient energy to the adjacent tissue to form a desired lesion. If the gap between the catheter and the tissue becomes too great, an undesirable amount of the ablation energy may pass to the blood rather than to the tissue. Also, if the conductive fluid medium flows out the portholes at too high of a flow rate, the composition of the patient's blood may be adversely effected by the excess quantity of conductive fluid medium being mixed with the patient's blood.

The desired flow rate of the conductive fluid medium is achieved by adjusting, for example, the pressure pushing the conductive fluid medium through the first lumen, changing the size of the first lumen, changing the finish on the inner wall of the first lumen, changing the size or distribution of the portholes, changing the cross-sectional configuration of the portholes, altering the spacing 100 (FIG. 7) between the portholes, and/or changing the porthole diameter gradient between the first porthole and the last porthole whenever such a gradient exists. Another factor that may be taken into account when adjusting the flow rate of the conductive fluid medium is the configuration of the porous conductor. For example, the size of the gaps or pores may be adjusted when trying to establish a satisfactory flow rate through the distal portion of the ablation catheter. The porous conductor may significantly restrict the flow of the conductive fluid medium from the portholes. A metal mesh electrode with a mesh gap size of about 10–50 micrometers may permit a desired flow rate of the conductive fluid medium, for example. The specific configuration of the distal portion of the ablation catheter can also influence the flow rate of the conductive fluid medium. For example, in the first embodiment of the ablation catheter (see, e.g. FIGS. 1–3), the radius of curvature of the active region 38 of the distal portion 18 affects the tendency of the conductive fluid medium 66 to flow out of the portholes 44–48.

Figure 12:
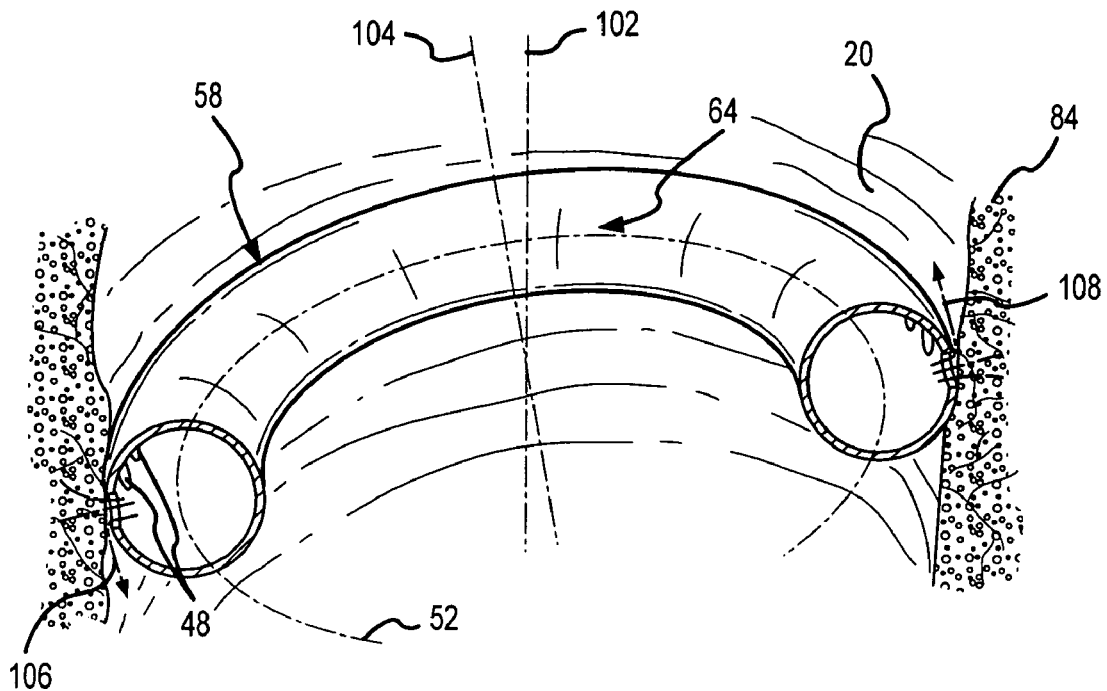
FIG. 12 is similar to FIG. 11, but depicts a section of the active region of the distal portion of an ablation catheter according to a third variant of the first embodiment of the present invention, wherein the active region has a circular cross section with a constant wall thickness.

FIG. 12 is a fragmentary, isometric view of a portion of the active region of an ablation catheter 10 according to a third variant of the first embodiment of the present invention. In this variant, the ablation catheter 10 has a circular cross section and walls of a constant thickness (compare FIG. 5 wherein the catheter wall has a thickened area 70), but the walls could be of a changing or variable thickness. This is a traditional, axisymmetric round extrusion. In FIG. 12, the ablation catheter is positioned to create a desired lesion, with the active region of the ablation catheter extending around or encircling the longitudinal axis 102 of a pulmonary vein, for example. With the ablation catheter in this position, the longitudinal axis 52 of the active region of the ablation catheter encircles the longitudinal axis 102 of the pulmonary vein. Since the internal anatomy of veins varies greatly, and since it is difficult to align the active region of the ablation catheter such that the longitudinal axis 102 of the pulmonary vein is precisely aligned with the longitudinal axis 104 of the catheter shaft 14, it is possible that the portholes 44–48 will not rest as directly against the internal surface 20 of the pulmonary vein as may be desired.

As shown in FIG. 12, this makes it possible for the active region to roll or move when placed on an irregular surface, which permits the conductive fluid medium and RF energy to asymmetrically exit the portholes as indicated by the arrows 106, 108 on FIG. 12 and to exit the portholes more easily than desired. This in turn can lead to less effective operation of the ablation catheter 10. In other words, when the portholes 44–48 through which the conductive fluid medium 66 exits the ablation catheter are pressed precisely and solidly against the internal surface of the pulmonary vein (e.g., the left superior pulmonary vein 84 shown in FIG. 12), a better lesion may be formed. On the other hand, when the outer peripheral wall 50 (see, e.g., FIGS. 3–5) of the ablation catheter rests on the internal surface of the pulmonary vein at an angle, as shown in FIG. 12, an opportunity is presented for the conductive fluid medium and RF energy to asymmetrically and easily escape from the region between the ablation catheter 10 and the tissue 20 comprising the inner wall of the pulmonary vein 84, producing a lower quality lesion. Thus, it is desirable to configure the active region of the distal portion of the ablation catheter such that the outer peripheral wall of the active region is biased against the tissue to be ablated.

FIGS. 13–19 depict cross-sectional configurations that are not completely axisymmetric about the longitudinal axis of the active region of the ablation catheter. These cross-sectional configurations are biased toward a preferred orientation that places the outer peripheral wall, and thus the active region of the catheter (e.g., the portholes, if present), squarely against the tissue to be ablated. When the outer peripheral wall is biased against the ostium or the inner wall of the pulmonary vein, the active region of the ablation catheter is easier to position and more stable during operation. If one or more portholes are present and conductive fluid medium is flowing through the portholes, manifolding of the conductive fluid medium is improved, and blood may be more effectively isolated from the tissue to be ablated.

Figure 13:
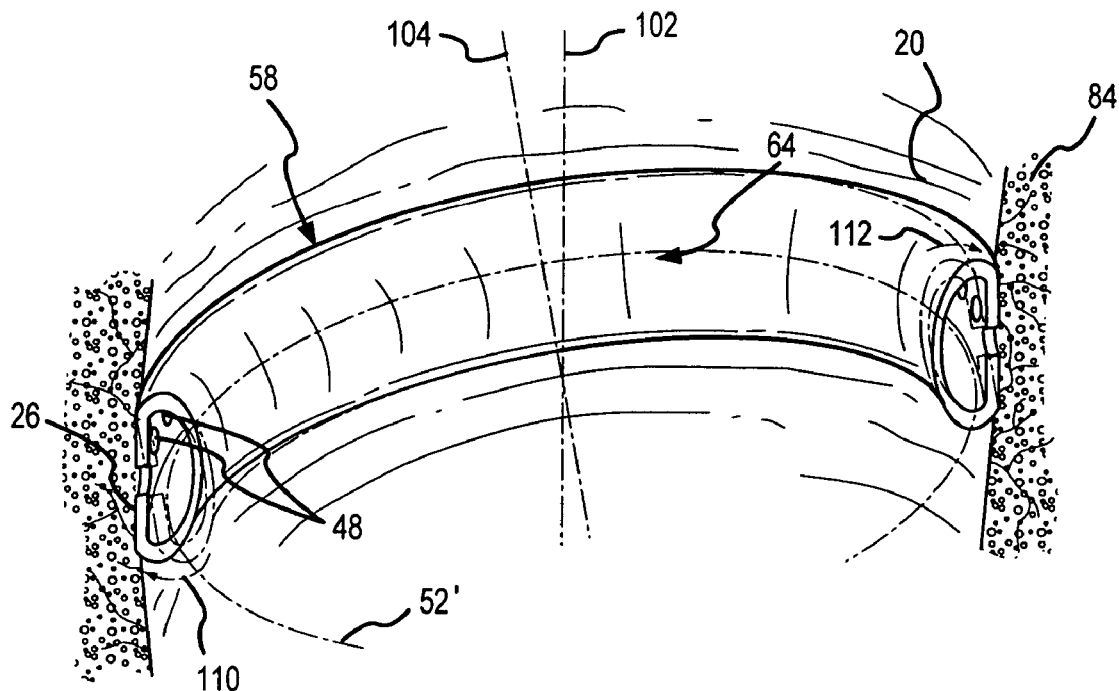
FIG. 13 is similar to FIG. 12, but depicts a section of the active region of the distal portion of an ablation catheter according to a fourth variant of the first embodiment of the present invention, wherein the active region has a D-shaped cross section with a constant wall thickness.
Figure 14:
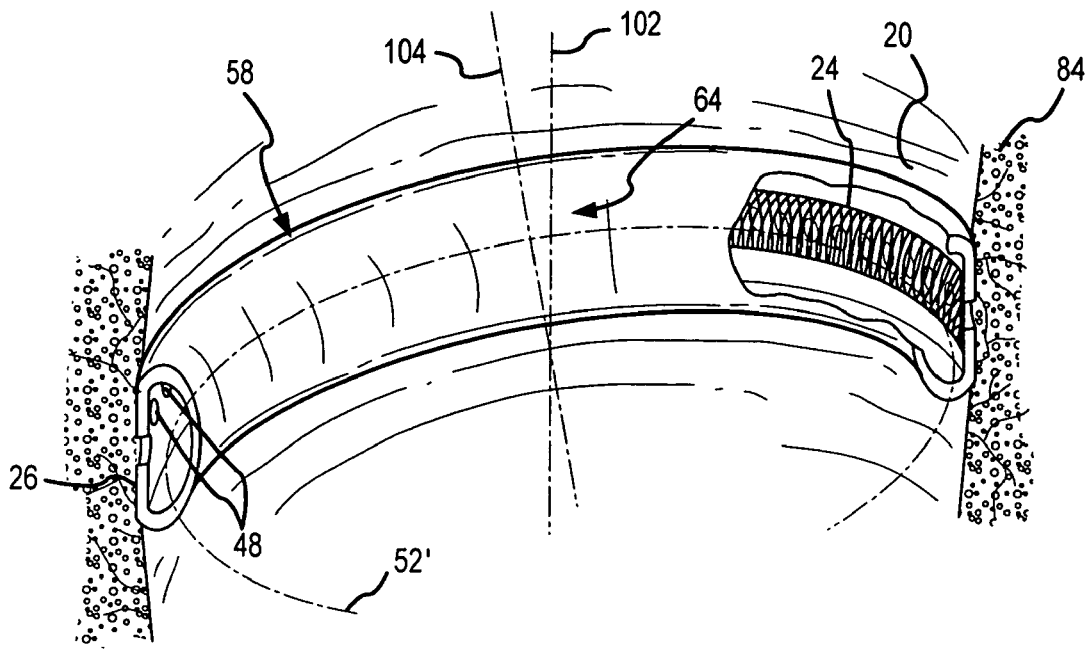
FIG. 14 is similar to the embodiment depicted in FIG. 13, but depicts a section of a distal portion of an ablation catheter according to a fifth variant of the first embodiment of the present invention, wherein the distal portion has a piece of the inner peripheral wall broken away to reveal a porous conductor in position over the portholes.

In the fourth and fifth variants of the first embodiment depicted in FIGS. 13 and 14, respectively, the active region of the ablation catheter has a D-shaped cross-section. As shown in FIG. 13, which depicts the fourth variant of the first embodiment (no porous conductor present), when the ablation catheter having this cross-sectional configuration first contacts the tissue to be ablated (phantom lines in FIG. 13), it is biased in the direction of the two curved arrows 110, 112 depicted in FIG. 13 to torque and rotate the entire outer peripheral wall 26 into direct contact with the tissue 20 to be ablated (solid lines in FIGS. 13 and 14). This cross-sectional configuration for the active region of the distal portion of the ablation catheter thus helps orient the outer peripheral wall 26 against the tissue 20 to be treated or diagnosed. In the depicted embodiment, portholes 44–48 pass through this outer peripheral wall 26. Thus, when the outer peripheral wall 26 is biased against the tissue 20 to be ablated, the portholes are best oriented to achieve the desired lesion. In FIG. 14, which depicts the fifth variant of the first embodiment, the D-shaped cross-sectional configuration is shown again, but a piece of the inner peripheral wall 64 has been broken out to reveal a porous conductor 24 in position in the lumen of the ablation catheter over the portholes. For the configuration depicted in FIGS. 13 and 14, an aspect ratio of at least 1.5:1 and preferably of 2.2:1 has been found to work well.

Figure 15:
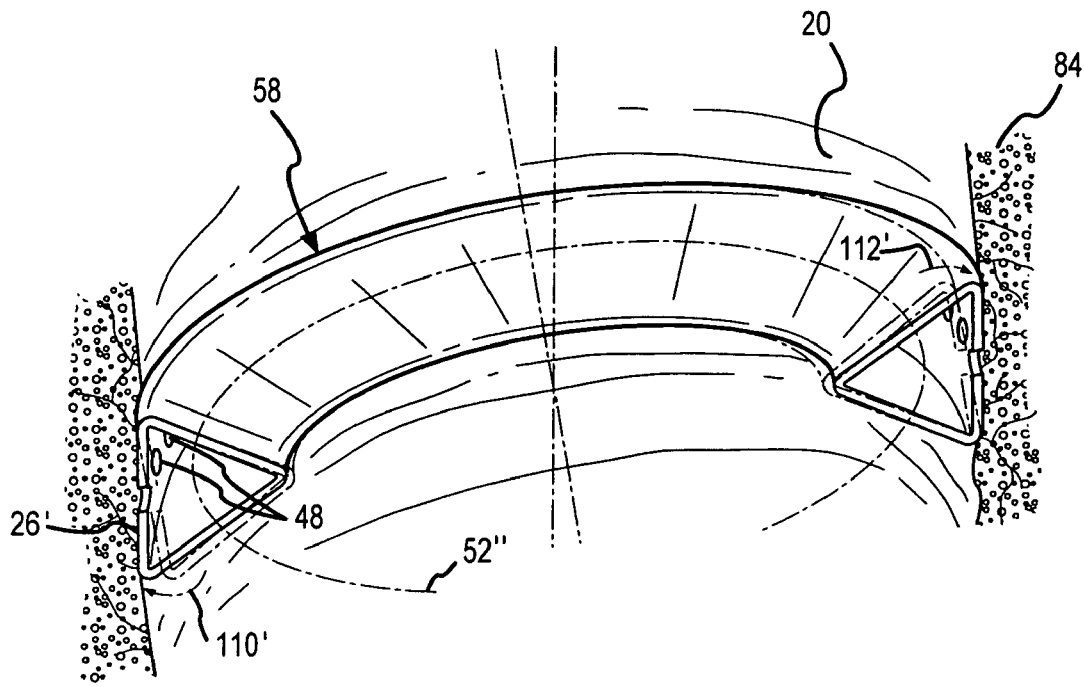
FIG. 15 is similar to FIG. 13, but depicts a section of a distal portion of an ablation catheter according to a sixth variant of the first embodiment of the present invention, wherein the active region of the distal portion has a triangular cross section.

FIG. 15 depicts a sixth variant of the first embodiment, which is another possible cross-sectional configuration for the active region of the distal portion of a catheter that would bias the outer peripheral wall 26' of the catheter against the tissue 20 to be diagnosed or treated (e.g., ablated). As shown in FIG. 15, when the active region first contacts the tissue 20 (phantom lines in FIG. 15), the outer peripheral wall 26' may not be as fully seated as possible against the tissue 20. The triangular cross-sectional configuration depicted in FIG. 15, however, again biases the outer peripheral wall 26' in the direction of the two curved arrows 110', 112' depicted in FIG. 15, to torque and rotate the entire outer peripheral wall 26' against the tissue 20, driving the distal portion 18 of the catheter 10 toward the orientation depicted in solid lines in FIG. 15. Other configurations that bias the outer peripheral wall against the tissue are possible and include any configurations that have a substantially flattened outer peripheral wall. For example, a rectangular cross-sectional configuration and other multi-side cross-sectional configurations that includes at least one flattened outer peripheral wall would also bias the outer peripheral wall against the tissue 20. As previously alluded to, the orientation biasing configurations (e.g., those depicted in FIGS. 13–15) may be used in devices with or without a fluid distribution manifold like the series of portholes 44–48 depicted in these figures.

Figure 16:
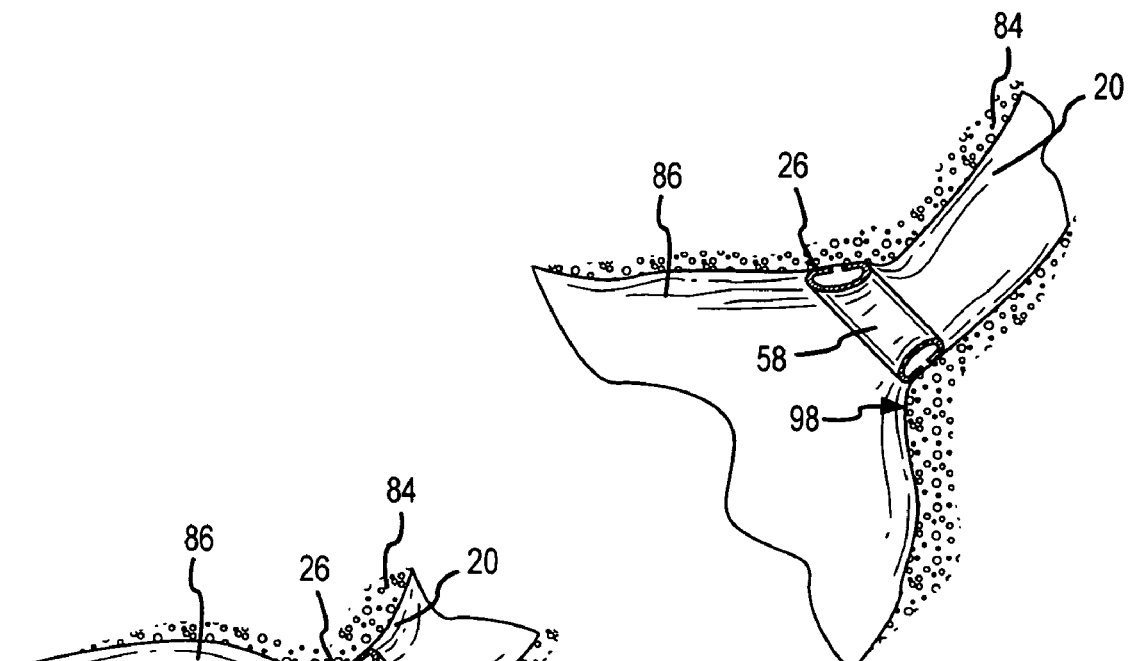
FIGS. 16–19 depict various fragmentary, cross-sectional views of portions of a pulmonary vein and portions of the left atrium, with a section of the ablation catheter embodiment depicted in FIG. 13 or FIG. 14 in place against the ostium or the inner wall of the pulmonary vein.
Figure 17:
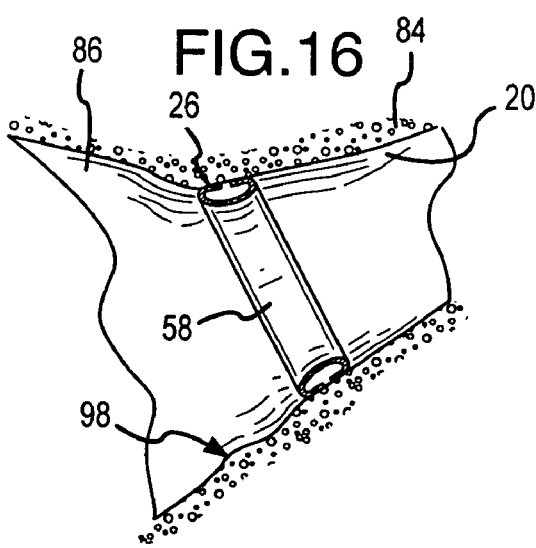
Figure 18:
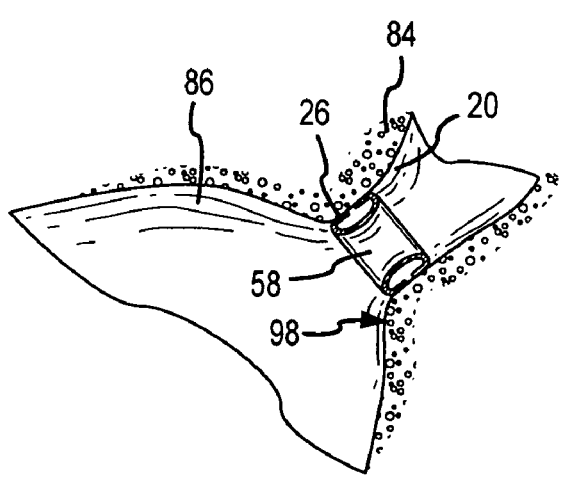
Figure 19:
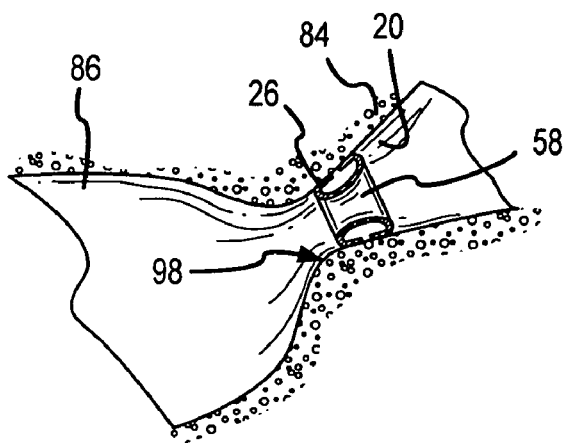

FIGS. 16–19 depict an ablation catheter having a cross-sectional configuration shown to best advantage in FIGS. 13 and 14 being used during pulmonary vein ablation. As shown in FIGS. 16–19, the ostium 98 of a pulmonary vein 84 may have a variety of irregular shapes. In FIG. 16, the side walls of the pulmonary vein 84 are substantially parallel, but the walls do not remain parallel adjacent to the ostium 98, where the pulmonary vein connects to the left atrium 86. As shown in FIG. 16, a catheter having a third curved section 58 with a biasing cross-sectional configuration (e.g., the D-shaped configuration depicted in this figure and FIGS. 13 and 14) is able to twist about the longitudinal axis 52' of the active region and about the longitudinal axis 104 of the catheter shaft 14, thereby better ensuring that the outer peripheral wall 26 of the distal portion of the ablation catheter is seated against the tissue 20 to be ablated. FIG. 17 depicts yet another possible anatomy for the pulmonary vein 84, ostium 98, and left atrium 86. In this figure, the side walls of the pulmonary vein diverge near the ostium. The active region of the distal portion is again biased against the inner wall of the pulmonary vein near the ostium 98 by the cross-sectional configuration of the active region. FIGS. 18 and 19 provide additional views of possible variations in the anatomy of a human heart, and, again, the active region of the distal portion of the ablation catheter is biased against the tissue 20 to be ablated. Clearly, there are as many possible heart anatomies as there are hearts.

The unique cross-sectional configurations depicted in FIGS. 13–19, having a flattened outer peripheral wall 26, 26' that enhances contact between the ablation catheter and the tissue to be ablated, are not limited to use with ablation catheters employing virtual electrodes like the porous conductor 24. The cross-sectional configurations depicted in FIGS. 13–19, could be used with ablation catheters that generate ablation energy by other than a porous conductor (e.g., a flat wire electrode and a coiled wire electrode). These biasing configurations enhance the performance of catheters having diagnostic or therapeutic electrodes, including actual electrodes (e.g., traditional ring electrodes), or virtual electrodes, or other energy sources that need to be accurately oriented relative to selected tissue.

Although FIGS. 13–19 are described in connection with an ablation catheter assembly, the unique cross-sectional configurations shown in these figures and discussed above for biasing an active region of a catheter against tissue could also be used with diagnostic catheters or other catheters that do not ablate tissue.

Although preferred embodiments of this invention have been described above with a certain degree of particularity, those skilled in the art could make numerous alterations to the disclosed embodiments without departing from the spirit or scope of this invention. For example, the porous conductor described above could be used with another electrical element. In such an embodiment, the mesh or weave may not distribute energy, thereby comprising, for example, a passive part of a fluid distribution manifold. In contrast, the porous conductor described above both comprises part of the fluid distribution manifold and distributes energy. Also, the drawings disclose a distal portion of the catheter that includes a plurality of circular portholes, but the portholes need not be circular, and a single, elongated porthole may be used in place of the depicted plurality of portholes. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation catheter for treating tissue, the ablation catheter comprising
   a porous conductor adapted to deliver therapeutic energy; and a catheter shaft having a proximal portion and a distal portion, wherein said distal portion comprises at least one lumen adapted to carry wires, optical fibers, and fluids for a variety of functional purposes, wherein said porous conductor is attached within said at least one lumen; and an active region, wherein said active region includes a plurality of portholes adapted to introduce the therapeutic energy from said porous conductor to the tissue, and wherein said active region has a cross-sectional configuration that includes a flattened outer peripheral wall.

2. The ablation catheter of claim 1, wherein said catheter shaft is constructed from a polymer, and wherein said porous conductor is constructed from metal mesh.

3. The ablation catheter of claim 1, wherein said at least one lumen comprises at least a first lumen, wherein said first lumen is adapted to carry a conductive fluid medium from said proximal portion to said plurality of portholes along said active region, wherein said porous conductor is attached within said first lumen over said plurality of portholes, and wherein said porous conductor is adapted to supply the therapeutic energy to the tissue through said conductive fluid medium.

4. The ablation catheter of claim 1, wherein said distal portion has an outer peripheral wall, wherein said active region has a longitudinal axis, and wherein said plurality of portholes are arranged along a porthole centerline extending along said outer peripheral wall parallel to said longitudinal axis of said active region.

5. The ablation catheter of claim 1, wherein said at least one lumen further comprises a second lumen, and wherein a shape retention wire is mounted in said second lumen.

6. The ablation catheter of claim 1, wherein said porous conductor is a metal mesh electrode.

7. The ablation catheter of claim 1, wherein said catheter shaft has a cross-sectional configuration that includes at least one thickened areas.

8. The ablation catheter of claim 1, wherein said cross-sectional configuration of said active region is a polygonal configuration having said flattened outer peripheral wall.

9. The ablation catheter of claim 8, wherein said polygonal configuration is selected from the group consisting of a D-shaped configuration, a triangular configuration, and a rectangular configuration.

10. The ablation catheter of claim 1, wherein said at least one lumen further comprises a second lumen, and wherein a shape retention means for biasing said distal portion toward a predetermined shape is mounted in said second lumen.

11. The ablation catheter of claim 10, wherein said shape retention means comprises a Nitinol wire.

12. The ablation catheter of claim 10, wherein said shape retention means comprises a super elastic wire.

13. An ablation catheter for treating tissue, the ablation catheter comprising a catheter shaft, said catheter shaft comprising a proximal portion;

a distal portion, said distal portion being adapted to be inserted into a body cavity having tissue to be ablated, said distal portion comprising a looped structure transverse to a longitudinal axis of said catheter shaft, and said distal portion comprising an active region including at least one porthole adapted to deliver a conductive fluid medium to the tissue; and a first lumen extending from said proximal portion to said distal portion, said first lumen being adapted to carry said conductive fluid medium from said proximal portion to said at least one porthole along said active region of said distal portion; and a mesh electrode mounted within said first lumen over said at least one porthole and extending along said active region of said distal portion, wherein said mesh electrode is adapted to supply ablation energy to the tissue through the conductive fluid medium.

14. The ablation catheter of claim 1, wherein said distal portion is straight.

15. The ablation catheter of claim 13, wherein said distal portion comprises a first curved section, a second curved section, and a third curved section, and wherein said third curved section defines said looped structure and said active region.

16. The ablation catheter of claim 15, wherein said at least one porthole comprises a plurality of portholes arranged along a porthole centerline, and wherein said looped structure has an outer peripheral wall, and wherein said active region is along a radial apex of said outer peripheral wall, along said porthole centerline.

17. The ablation catheter of claim 13, wherein said catheter shaft is a braided shaft.

18. The ablation catheter of claim 13, wherein said distal portion has a cross-sectional configuration along said active region, and wherein said cross-sectional configuration is adapted to bias said active region against the tissue.

19. The ablation catheter of claim 18, wherein said cross-sectional configuration along said active region is a polygonal configuration having a flattened outer peripheral wall.

20. The ablation catheter of claim 19, wherein said polygonal configuration is selected from the group consisting of a D-shaped configuration, a triangular configuration, and a rectangular configuration.

21. An ablation catheter for ablating tissue, the ablation catheter comprising a catheter shaft, said catheter shaft comprising a proximal portion;

a distal portion comprising at least one curved section adapted to be inserted into a body cavity having tissue to be ablated, wherein said at least one curved section defines an inner peripheral wall and an outer peripheral wall, and wherein said outer peripheral wall has an active region that includes a plurality of portholes;

a first lumen extending from said proximal portion to said distal portion, said first lumen being adapted to carry a conductive fluid medium from said proximal portion to said portholes along said active region of said distal portion; and a second lumen extending adjacent to said inner peripheral wall;

a mesh electrode mounted within said first lumen over said plurality of portholes and extending along said active region of said distal portion, wherein said mesh electrode is adapted to supply ablation energy through the conductive fluid medium; and a shape retention means mounted in said second lumen for biasing said distal portion toward a predetermined shape.

22. The ablation catheter of 21, wherein said distal portion has a cross-sectional configuration along said active region, and wherein said cross-sectional configuration is adapted to bias said active region against the tissue.

23. The ablation catheter of claim 22, wherein said cross-sectional configuration along said active region is a polygonal configuration having a flattened outer peripheral wall.

24. The ablation catheter of claim 23, wherein said polygonal configuration is selected from the group consisting of a D-shaped configuration, a triangular configuration, and a rectangular configuration.

* * * * *